United States Patent [19]

McLaren

[11] Patent Number: 5,053,035
[45] Date of Patent: Oct. 1, 1991

[54] FLEXIBLE INTRAMEDULLARY FIXATION ROD

[76] Inventor: Alexander C. McLaren, 122 Whiteacres Dr., London, Ontario, Canada, N6G 4E8

[21] Appl. No.: 528,590

[22] Filed: May 24, 1990

[51] Int. Cl.⁵ .................................. A61B 17/58
[52] U.S. Cl. .................................. 606/67; 606/62
[58] Field of Search ............ 606/60, 62, 66, 63, 606/64, 67, 68

[56] References Cited

U.S. PATENT DOCUMENTS

| | | | |
|---|---|---|---|
| 2,518,019 | 8/1950 | Kane | 128/92 |
| 3,208,450 | 9/1965 | Abelson | 128/83 |
| 3,463,158 | 8/1969 | Schmitt et al. | 128/334 |
| 3,530,854 | 9/1970 | Kearney | 128/92 |
| 3,678,925 | 7/1972 | Fischer et al. | 128/92 |
| 3,709,218 | 1/1973 | Halloran | 128/92 |
| 3,716,051 | 2/1973 | Fischer | 128/92 |
| 3,717,146 | 2/1973 | Halloran | 128/92 |
| 3,739,773 | 6/1973 | Schmitt et al. | 128/92 |
| 3,760,802 | 9/1973 | Fischer et al. | 128/92 |
| 3,763,855 | 10/1973 | McAtee | 128/92 |
| 3,783,860 | 1/1974 | Burstein et al. | 128/92 |
| 3,892,233 | 7/1975 | Vestby | 606/67 |
| 3,893,196 | 7/1975 | Hochman | 3/1.91 |
| 3,977,398 | 8/1976 | Burstein | 128/92 |
| 3,990,438 | 11/1976 | Pritchard | 128/92 |
| 4,055,172 | 10/1977 | Ender et al. | 128/92 |
| 4,091,806 | 5/1978 | Aginsky | 128/92 |
| 4,103,683 | 8/1978 | Neufeld | 128/92 |
| 4,135,507 | 1/1979 | Harris | 128/92 |
| 4,169,470 | 10/1979 | Ender et al. | 128/92 |
| 4,204,531 | 5/1980 | Aginsky | 128/92 |
| 4,212,294 | 7/1980 | Murphy | 128/92 |

(List continued on next page.)

FOREIGN PATENT DOCUMENTS

| | | | |
|---|---|---|---|
| 480652 | 2/1977 | Australia | 606/62 |
| 757951 | 11/1953 | Fed. Rep. of Germany | 606/67 |
| 2221111 | 10/1974 | France | 606/62 |
| 8101647 | 6/1981 | World Int. Prop. O. | 606/62 |

OTHER PUBLICATIONS

Slide presentation given 05/28/89 at Canadian Conference of Orthopaedic Surgeons.
Excerpts of article handed out 05/28/89 at Canadian Conference of Orthopaedic Surgeons discussing use of fixation rods for treating fractured bones.
Sales brochures excerpts for fluted intramedullary rods distributed by 3M (Minnesota Mining & Mfg. Co.)

Primary Examiner—Robert A. Hafer
Assistant Examiner—Kevin G. Rooney
Attorney, Agent, or Firm—Limbach, Limbach & Sutton

[57] ABSTRACT

A flexible inramedullary fixation rod for fractured bones is provided having a length sufficient to extend a substantial distance on either side of a diaphyseal fracture site and a substantially circular core with radially disposed fins extending substantially along the full length thereof. The radii of the core and fins are such that the rod can pass through the bone's medullary canal and engage the inner, or endosteal, surface of the bone along line contacts, thereby allowing normal endosteal healing and intramedullary revascularization. The rod is constructed of a flexible, bio-compatible material, such as titanium, stainless steel, resorbable polymers (e.g., polylactic acid) or carbon fiber-polysulfone. The radii of the fins are selected to be substantially equal to the minimum radius of the medullary canal. The core radius is selected in accordance with the Young's and shear moduli associated with the bio-compatible material to provide a rod structural rigidity (bending and torsional) preferably between 0.1% and 10% of the inherent bone rigidity with the relationship between the rod bending and torsional rigidities preferably being substantially the same as the corresponding relationship for the intact bone. This causes natural stresses (bending and torsional) to be maintained at the fracture site, thereby promoting natural and therefore stronger healing of the fractured bone.

10 Claims, 2 Drawing Sheets

U.S. PATENT DOCUMENTS

| | | | |
|---|---|---|---|
| 4,227,518 | 10/1980 | Aginsky | 128/92 |
| 4,237,875 | 12/1980 | Termanini | 128/92 |
| 4,275,717 | 6/1981 | Bolesky | 128/92 |
| 4,281,649 | 8/1981 | Derweduwen | 128/92 |
| 4,313,434 | 2/1982 | Segal | 128/92 |
| 4,446,579 | 5/1984 | Inamori et al. | 3/1.91 |
| 4,452,973 | 6/1984 | Casey et al. | 528/354 |
| 4,457,301 | 7/1984 | Walker | 128/92 |
| 4,473,069 | 9/1984 | Kolmert | 128/92 |
| 4,475,545 | 10/1984 | Ender | 128/92 |
| 4,522,202 | 6/1985 | Otte et al. | 128/92 |
| 4,541,424 | 9/1985 | Grosse et al. | 128/92 |
| 4,574,795 | 3/1986 | Georges | 128/92 |
| 4,621,628 | 11/1986 | Brudermann | 128/92 |
| 4,622,959 | 11/1986 | Marcus | 128/92 |
| 4,628,920 | 12/1986 | Mathys, Jr. et al. | 128/92 |
| 4,632,101 | 12/1986 | Freedland | 128/92 |
| 4,667,664 | 5/1987 | Taylor et al. | 128/92 |
| 4,697,585 | 10/1987 | Williams | 128/92 |
| 4,705,027 | 11/1987 | Klaue | 128/92 |
| 4,756,307 | 7/1988 | Crowninshield | 606/67 |
| 4,776,330 | 10/1988 | Chapman et al. | 128/92 |
| 4,805,607 | 2/1989 | Engelhardt et al. | 606/67 |
| 4,827,917 | 5/1989 | Brumfield | 128/42 |
| 4,846,162 | 7/1989 | Moehring | 128/92 |
| 4,854,312 | 8/1989 | Raftopoulos et al. | 128/92 |
| 4,858,602 | 8/1989 | Seidel et al. | 128/92 |
| 4,875,474 | 10/1989 | Border | 128/92 |
| 4,875,475 | 10/1989 | Comte et al. | 128/924 |
| 4,877,019 | 10/1989 | Vives | 128/92 |
| 4,881,535 | 11/1989 | Sohngen | 606/98 |

FLEXIBLE INTRAMEDULLARY FIXATION ROD

BACKGROUND OF THE INVENTION

1. Field of the Invention

This invention relates generally to devices and methods for setting fractured long bones of the body, such as arm and leg bones. More particularly, this invention relates to an improved intramedullary fixation rod for setting a fractured bone in a manner permitting limited elastic movement in response to natural stresses at the fracture site to avoid interference with the natural healing process.

2. Description of the Related Art

Long bones of the body are characterized by a combination of two different bone materials cooperating together to provide a relatively lightweight and high load bearing structure. More specifically, such bones consist of a relatively hard and generally tubular outer layer of cortical bone, sometimes referred to as the cortex, encasing a considerably softer and sponge-like inner bone material referred to as cancellous bone. Examples of such long bones in the human body are leg bones including the femur, tibia, and fibula, as well as arm bones including the radius, ulna, and humerus.

When a long bone is diaphyseally fractured, it is necessary to set the fracture by returning or reducing the adjacent broken bone ends at the fracture site to their original anatomical positions. The fractured bone is then restrained or fixed in the reduced position by an appropriate restraining device thereby permitting healing to proceed. The restraining device must be left in place at least until the fracture is substantially healed.

A variety of restraining devices and placement procedures therefor are known for maintaining diaphyseal fractures in long bones in a reduced position. For example, fixation plates have been used conventionally for many years and are placed surgically onto the bone in a position spanning the fracture site. Screws or other suitable attachment devices are fastened through the plate into the bone to lock the plate in position and thereby rigidly immobilize the fracture site for an extended period of time during which the bone is allowed to heal.

However, such fixation plates isolate the fracture site from natural stresses and interfere with callus formation, thereby interfering with the natural healing process. As a result, the cortical bone in the region of the fracture site tends to heal with undesirable cancellization of the cortical bone, thus providing a relatively weak bone structure subject to refracture. Furthermore, the formation of screw holes in the cortical bone provides stress risers which further substantially increase the risk of bone refracture. Moreover, relatively complicated surgical procedures are required for the implantation and subsequent removal of such fixation plates, thereby presenting significant risks of neurovascular injury and resulting in substantial emotional trauma to the patient.

Alternative fracture restraining devices have been proposed in the form of intramedullary fixation rods or nails for fixation of the bone fracture without requiring use of fixation plates. Such fixation rods have been provided in various lengths and cross-sectional shapes for insertion through the medullary canal of a fractured bone to support adjacent broken bone ends in alignment with each other during healing.

In general, these fixation rods fill the intramedullary canal and have substantial contact with the inner, or endosteal, surface of the cortical bone. This inhibits endosteal callus formation and revascularization of the bone by its endosteal blood supply.

Furthermore, these fixation rods have generally provided relatively poor rotational stability, particularly in response to any relative rotation between the broken bone ends, thereby tending to result in undesired rod loosening.

Moreover, these fixation rods have consisted of relatively rigid structures insertable only into relatively straight bones, such as the femur. These rods function to rigidly immobilize the fracture site throughout the healing process. This results in shielding the fracture from natural loading stresses and inhibiting callus formation, thus promoting a relatively poor healing of the fracture. Furthermore, fixation rods currently available have relationships between their bending and torsional rigidities which are substantially different from those of intact bone. This can result in rigid fixation in bending but unstable fixation in torsion.

Rods have been used through the medullary canal of a somewhat curved bone, such as the radius or ulna bones of the forearm. When installed, however, these fixation rods have functioned to straighten the fracture site, leading to malreduction or unsatisfactory positioning of the fracture fragments.

Therefore, a significant and important need exists for an improved device for reducing a diaphyseal fracture in a long bone in a manner which promotes callus formation and the natural healing process and allows normal endosteal healing. Furthermore, a need exists for such an improved device which can be installed or removed without complicated surgical procedures, which provides relatively high rotational stability and which can be used with curved bones, such as the radius or ulna of the forearm, as well as other long bones, such as the femur or tibia. The present invention fulfills these needs and provides further related advantages.

SUMMARY OF THE INVENTION

A flexible intramedullary fixation rod in accordance with the present invention provides for flexible fixation of a diaphyseal fracture of a bone in a manner which promotes more natural, and therefore faster and stronger healing. Its flexibility prevents undesirable shielding of the fracture from normal physiological stresses, instead allowing normal physiological stresses to be transmitted to the site of the bone fracture to stimulate healing and to prevent osteoporosis from developing.

A fixation rod in accordance with the present invention has an elongated shape with a cross-sectional profile having a core with multiple fins radially disposed about the periphery. These radially disposed fins have outer edges which extend parallel to and along the core longitudinal axis at a radial distance selected to allow insertion of the rod into the intramedullary canal of the fractured bone to be repaired. The length of the rod is selected to allow the rod to extend within the intramedullary canal, once installed, for a substantial distance on either side of the site of the diaphyseal fracture.

A flexible intramedullary fixation rod in accordance with the present invention is fabricated from an elastic material which gives the rod a structural rigidity which is a fraction of the structural rigidity of the intact bone (e.g., approximately 0.1%–10%). Furthermore, a fixation rod in accordance with the present invention has a structural rigidity with substantially the same relationship between its bending and torsional rigidities as the corresponding relationship between the bending and torsional rigidities of the intact bone.

A flexible intramedullary fixation rod in accordance with the present invention provides means by which the desired structural rigidity for the fixation rod can be selected for any given fabrication material. The radii of the outer edges of the fins are designed to allow the rod to pass through the medullary canal within the confines of the cortical bone structure. The radius of the fixation rod core is then selected, in accordance with the selected fin radii and the rod material's Young's modulus and shear modulus to provide a fixation rod having the structural rigidity (bending and torsional) less than the structural rigidity of the intact bone.

Thus, the radially disposed fins of the flexible intramedullary fixation rod in accordance with the present invention provide two substantial benefits. The radial extension of the fins provide an open cross-sectional shape which locks securely within the cancellous bone within the medullary canal of the fractured bone, thereby preventing excessive rotation of the fractured bone segments. Further, the radius of the core is selected, in accordance with the radial extension of the fins and the known physical characteristics of the rod fabrication material, to specifically provide the desired structural rigidity. This results in a fracture fixation technique in which the bone segments are anatomically aligned and experience normal, natural bending and torsional stresses without loss of bending or rotational rod fixation on either side of the fracture site. This promotes callus formation, thereby enhancing rapid and strong fracture healing.

These and other objectives, features and advantages of the present invention will be understood upon consideration of the following detailed description of the invention and the accompanying drawings.

BRIEF DESCRIPTION OF THE DRAWINGS

Throughout the figures, corresponding elements are designated with similar numerals.

DETAILED DESCRIPTION OF THE INVENTION

Figure 1:
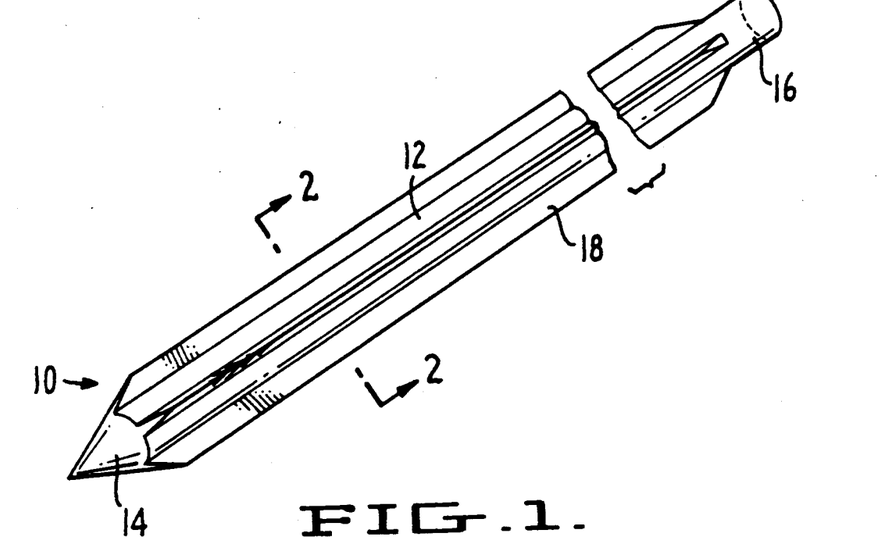
FIG. 1 illustrates a perspective view of a flexible intramedullary fixation rod in accordance with the present invention.

Referring to FIG. 1, a flexible intramedullary fixation rod 10 in accordance with the present invention is of unitary construction and has a central core 12 with an insertion end 14 and installation end 16. Radially disposed about the periphery of the core 12 are longitudinal fins 18. As described more fully below, the fabrication material and structural characteristics of the rod 10 allow it to be driven through the medullary canal of a bone having a diaphyseal fracture to span the fracture site to support and to maintain alignment of the adjacent broken bone ends during their healing process. The insertion tip 14 is centrally pointed for ease of driving passage through the medullary canal without requiring prior reaming of a passage for the rod 10. The installation end 16 can be configured for coupling to any of several appropriate drive or removal tools (not shown) which are well known in the art. For example, the installation end 16 can consist of a female threaded socket or a male threaded shaft for coupling to a slap hammer.

The fixation rod 10 can be fabricated from any of several well known materials which will provide the rod 10 with sufficient elasticity to permit the rod 10 to be driven through the medullary canal of a relatively straight bone, such as the femur, or to follow the contoured medullary canal of a more curved bone, such as the radius or ulna of the forearm. These fabrication materials also provide substantially non-plastic deformation for recoil to the original, unstressed geometry upon removal of external stresses to prevent angulation or malrotation of the broken bone ends during the healing process. Such rod fabrication materials include, without limitation, titanium, stainless steel (e.g., surgical grade 316L), resorbable polymers (e.g., polylactic acid), carbon fiber-polysulfone or other composite materials.

As will be recognized by the ordinary artisan, the insertion end 14 need not be fabricated from the same flexible material as the remainder of the rod 10. For example, the insertion end 14 can be formed from a material whose structural rigidity is substantially greater than that required of the remaining portion of the fixation rod 10. The insertion end 14, for example, can be fabricated as a separate metal tip which is fastened onto the fixation rod structure, or the metal tip is formed by applying a metal coating over the insertion end 14 of the fixation rod structure.

Figure 2:
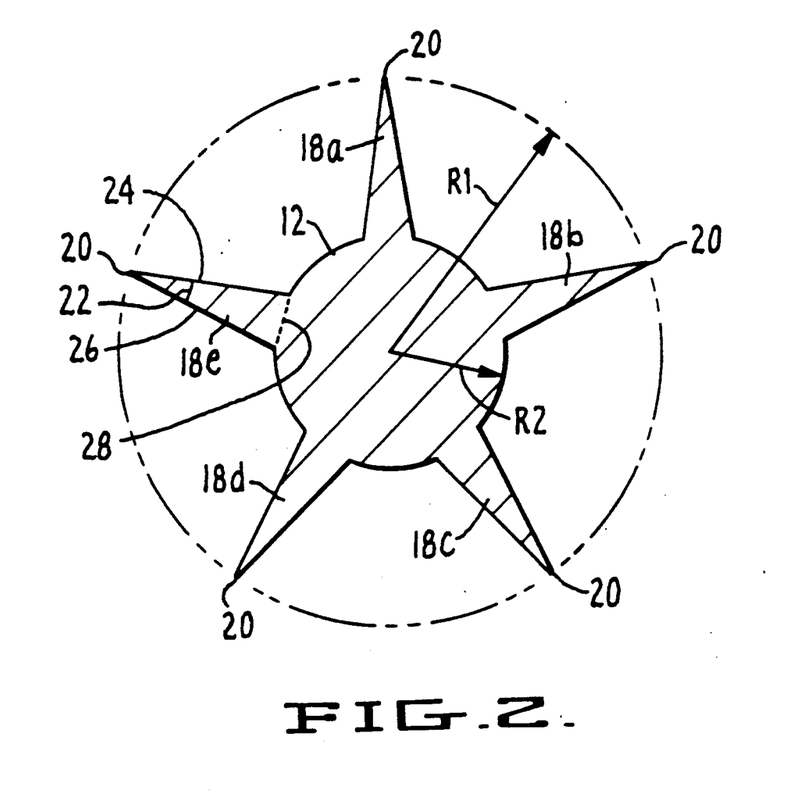
FIG. 2 illustrates a cross-sectional view of a flexible intramedullary fixation rod in accordance with the present invention.

FIG. 2 illustrates a cross-sectional view of the fixation rod 10 at line 2—2 of FIG. 1. The core 12 has a substantially circular cross-sectional area with a radius R2. Radially disposed about the periphery of the core 12 are five fins 18. The outer edges 20 of the fins 18 define a circle having a radius of R1. In other words, the outer edge 20 of each fin 18 lies at a radial distance R1 away from the center, i.e., the longitudinal axis, of the core 12.

The cross-sectional configuration of the rod 10 need not necessarily be completely symmetrical, depending upon the particular application. For example, the core 12 could be oval, or some other rotationally asymmetrical shape, and the outer edges 20 of the fins 18 could define an oval rather than a circle, or some other rotationally asymmetrical shape.

The radial extension R1 of the outer edges 20 of the fins 18 is selected so that the rod is to be received within the inner diameter of the cortical bone structure of the fractured bone. The radial extension R1 is selected so that the outer edges 20 of the fins 18 contact, without injuring, the inner surface of the cortical bone structure. The outer edges 20 are pointed so as to minimize surface contact between the rod 10 and the cortical bone structure, thereby minimizing any potential damage to the cortical bone structure or to its blood supply, and to allow normal endosteal healing and endosteal revascularization. However, the outer edges 20 should be slightly rounded (e.g., with a radius of approximately 0.15 mm), to prevent injury to the soft tissues at the insertion site.

As illustrated in FIG. 2, the fins 18 each have a substantially triangular cross-sectional area. At the outer edge 20 of each fin 18, an included, acute angle 22 separates the two outer surfaces 24, 26 and lies opposite the base 28 of the fin 18. In a preferred embodiment of the fixation rod of the present invention, this acute angle 22 is approximately 25°. However, this angle 22 can be varied, just as the cross-sectional area of each fin 18 may be other than triangular, without departing from the intended scope of the present invention.

As further illustrated in FIG. 2, five fins 18 are used on the presently preferred fixation rod 10 of the present invention. However, virtually any number of fins 18 greater than two can be used on a fixation rod 10 in accordance with the present invention. As long as three or more fins 18 are used, the fixation rod 10 will remain centrally located and supported within the medullary canal upon its implantation due to the interaction of the outer edges 20 of the fins 18 with the inner surface of the cortical bone structure.

The greater the number of fins 18 that are used, the greater the interdigitation of the fins 18 with the cancellous bone material. Further, the more fins 18 that are used, the smaller the included angle 22 and the shorter the base 28 become for each fin 18. Further still, in accordance with computations described more fully below, the more fins 18 that are used, the smaller the radius R2 of the core 12 needs to be for a given set of bending and torsional rigidities for the rod 10.

In a preferred embodiment five fins 18 are used to provide an asymmetrical cross-sectional shape having a substantially more consistent area moment of inertia about its periphery. This helps to inhibit torsional rotation, or twisting, of the rod 10 when it is flexed or bent.

The radius R2 of the periphery of the core 12 of the fixation rod 10 is determined in accordance with the desired structural rigidity of the fixation rod 10. This desired structural rigidity is less than the structural rigidity of the intact bone in which it is to be inserted. Once the radial extension R1 of the outer edges 20 of the fins 18 has been established, based upon the inside diameter of the cortical portion of the fractured bone, as discussed above, and once the fabrication material of the rod 10 is known, the radius R2 of the core 12 can be selected to provide the desired bending and torsional rigidities of the fixation rod 10.

The bending and torsional rigidities of a bone are directly related to the inside and outside diameters of its cortical bone structure, thereby allowing the bending and torsional rigidities of a bone to be empirically determined by calculations based upon dimensional measurements of the bone. Furthermore, the bending and torsional rigidities of a bone can be empirically determined by direct measurement thereof using instruments known and used in the art. Therefore, the bending and torsional rigidities of various bones can be predetermined.

For example, typical inside and outside diameters and bending and torsional rigidities for human femurs are shown in Table 1 below:

TABLE 1

| Typical Femur Characteristics | | | |
|---|---|---|---|
| Inner Diameter [mm] | Outer Diameter [mm] | Bending Rigidity [(N-m)/m] | Torsional Rigidity [(N-m)/r] |
| 17 | 29 | 20.0 × 10⁴ | 200 |
| 16 | 28 | 17.5 × 10⁴ | 180 |
| 15 | 27 | 15.5 × 10⁴ | 150 |
| 14 | 26 | 13.0 × 10⁴ | 130 |
| 13 | 25 | 11.5 × 10⁴ | 115 |
| 12 | 24 | 10.0 × 10⁴ | 100 |

TABLE 1-continued

| Typical Femur Characteristics | | | |
|---|---|---|---|
| Inner Diameter [mm] | Outer Diameter [mm] | Bending Rigidity [(N-m)/m] | Torsional Rigidity [(N-m)/r] |
| 11 | 23 | 8.5 × 10⁴ | 85 |
| 10 | 22 | 7.0 × 10⁴ | 70 | where: mm = millimeters
(N-m)/m = Newton-meters per meter
(N-m)/r = Newton-meters per radian Once the inside diameter of a fractured bone's cortical bone structure is known, the radial extension R1 of the edges 20 of the fins 18 and the bending and torsional rigidities of the bone therefore become known, leaving only the radius R2 of the core 12 to be determined. This radius R2 of the core 12 is selected to provide the desired bending and torsional rigidities of the fixation rod 10.

The bending and torsional rigidities of the fixation rod 10 are selected so as to have the same physiological relationship as those of the intact bone. In other words, the ratio of the bending rigidity to the torsional rigidity for the rod 10 is selectively set to be substantially equal to the ratio of the bending rigidity to the torsional rigidity for the intact bone. This has the effect of making the ratio of the rod 10 and bone bending rigidities equal to the ratio of the rod 10 and bone torsional rigidities.

The optimal structural rigidity of a fixation rod 10 in accordance with the present invention is between 0.1% and 10% of the structural rigidity of the intact bone. A fixation rod 10 having structural rigidity greater than 10% of the rigidity of the intact bone can be used, but is surgically less forgiving and tends to shield the fracture from otherwise normal stresses conducive to its healing. Similarly, a fixation rod 10 having a structural rigidity of less than 0.1% of the structural rigidity of the intact bone can also be used, but it can potentially allow excessive bending and torsional movement at the fracture site, thereby causing malunion and greater patient discomfort. However, depending upon the particular circumstances, a fixation rod having structural rigidity outside the range of 0.1%-10% e.g. 0.1%-15% can be designed and used. Furthermore, also depending upon the particular circumstances, the ratio of the rod 10 and bone bending rigidities need not necessarily be equal to the ratio of the rod 10 and bone torsional rigidities.

As discussed above, the normal bending and torsional rigidities of the fractured bone can be predetermined empirically and the desired bending and torsional rigidities of the fixation rod 10 can be selected accordingly. If the inside and outside radii of the cortical bone structure have been measured, the normal bending and torsional rigidities of the fractured bone can be determined by the following formulas:

$$E_B I_B = \frac{\pi}{4} (R_O{}^4 - R_I{}^4) E_B$$

$$K_B G_B = \frac{\pi}{2} (R_O{}^4 - R_I{}^4) G_B$$

where:
$E_B I_B$ = bending rigidity of bone
$K_B G_B$ = torsional rigidity of bone
$E_B$ = Young's modulus for cortical bone (typically $20 \times 10^3$ N/mm²)

$I_B$ = area moment of inertia of bone
$K_B$ = polar moment of inertia of bone
$G_B$ = shear modulus for cortical bone (typically $3.28 \times 10^3$ N/mm$^2$)
$R_O$ = outside radius of bone
$R_I$ = inside radius of bone If bending and torsional rigidities data are available based upon direct measurements of similar bones, the normal bending and torsional rigidities of the fractured bone can be determined by the following formulas:

$$E_B I_B = \frac{FL^3}{48D}$$

$$K_B G_B = \frac{TL}{A}$$

where:
F = linear deflection load force
L = length of bone
D = linear deflection
T = torsional deflection load force
A = angular deflection (radians)

Once the bending and torsional rigidities of the bone are known, the desired bending and torsional rigidities of the rod 10, which are to be proportional to the bending and torsional rigidities of the bone, can be selected (e.g., 6% of the structural rigidities of the bone). As discussed above, the fin radii R1 are selected in accordance with the minimum radius of the medullary canal. Then, once the bending and torsional rigidities for the rod 10 are selected, the core radius R2 can then be computed based upon the selected fin radii R1.

The desired bending and torsional rigidities of the rod 10 are computed according to the following formulas:

$$E_R I_R = R\%(E_B I_B)$$

$$K_R G_R = R\%(K_B G_B)$$

where:
$E_R I_R$ = bending rigidity of rod 10
$K_R G_R$ = torsional rigidity of rod 10
$E_R$ = Young's modulus for rod 10 (see Table 2)
$I_R$ = area moment of inertia of rod 10
$K_R$ = polar moment of inertia of rod 10
$G_R$ = shear modulus for rod 10 (see Table 2)
$R\%$ = ratio (in percent) of rod 10 rigidity to bone rigidity

TABLE 2

| | Typical Elasticity Moduli | |
|---|---|---|
| Rod Material | Young's Modulus (E) ($\times 10^4$ N/mm$^2$) | Shear Modulus (G) ($\times 10^4$ N/mm$^2$) |
| Titanium | 10.69 | 4.48 |
| Titanium 6AL4V | 11.03 | 4.28 |
| Stainles Steel 316L | 17.93 | 7.58 |
| Cobalt Chrome | 19.86 | 7.65 |
| Aluminum 2024 | 7.24 | 2.76 |
| Polylactic Acid | 3.00 | 1.20 |

Solving for the moments of inertia $I_R$, $K_R$ for the rod 10:

$$I_R = \frac{R\% (E_B I_B)}{E_R}$$

$$K_R = \frac{R\% (K_B G_B)}{G_R}$$

The area $I_R$ and polar $K_R$ moments of inertia for the rod 10 are computed according to the following formulas:

$$I_R = I_C + I_{F1} + I_{F2} + I_{F3} + I_{F4} + I_{F5}$$

$$K_R = K_C + K_{F1} + K_{F2} + K_{F3} + K_{F4} + K_{F5}$$

but:

$$K_R = K_C + 5K_F$$

where:
$I_c$ = area moment of inertia for core 12
$I_{Fn}$ = area moment of inertia for each fin 18 (where n $\epsilon\{1,2,3,4,5\}$)
$K_c$ = polar moment of inertia for core 12
$K_{Fn}$ = polar moment of inertia for each fin 18
$K_F = K_{Fn}$ for identical fins 18

The area $I_G$, $I_F$ and polar $K_c$, $K_c$ moments of inertia for the core 12 and fins 18 of the rod 10 can be computed, according to the following formulas:

$$I_C = \frac{\pi}{4} (R2)^4$$

$$I_F = I_{F1} + I_{F2} + I_{F3} + I_{F4} + I_{F5}$$

$$= I_{F1} + \sum_{n=2}^{5} I_{Fn}$$

where:

$$I_{F1} = (1/18)(R1 - R2)^4 \text{TAN}(\theta/2) +$$
$$(R1 - R2)^2 \text{TAN}(\theta/2) [(R1 + 2R2)/3]^2$$

$$I_{Fn} = (7/144)(R1 - R2)^4 \text{TAN}(\theta/2) +$$
$$(1/144)(R1 - R2)^4 \text{TAN}(\theta/2) |\text{COS}[2(n-1)\beta]| +$$
$$(R1 - R2)^2 \text{TAN}(\theta/2) [(5/3)(R2 - R1)\text{SIN}((n-1)\beta)]^2$$

and:

$$K_C = \frac{\pi}{2} (R2)^4$$

$$K_F = \frac{[2(R1 - R2)\text{TAN}(\theta/2)]^3 (R1 - R2)^3}{15 [2(R1 - R2)\text{TAN}(\theta/2)]^2 + 20 (R1 - R2)^2}$$

where:
$\beta$ = angle of rotation about periphery of core 12 separating fins 18
($\beta$ = 72 degrees for five fins 18)
COS (2n$\beta$) = cosine function of an angle of 2n$\beta$ degrees
SIN $\beta$ = sine function of an angle of $\beta$ degrees
$\theta$ = included angle 22 of fin 18
TAN $\theta/2$ = tangent function of an angle of $\theta/2$ degrees
R1 = fin radii (selected as discussed above)
R2 = core radius By substituting the area $I_c$, $I_F$ and polar $K_c$, $K_F$ moments of inertia for the oore 12 and fins 18 in the above expressions for the area $I_R$ and polar $K_R$ moments of inertia for the rod 10, the above equations for the desired bending and torsional rigidities of the rod 10 can be solved simultaneously to find the core radius R2. Such a simultaneous solution of two equations for two unknowns can be accomplished by any of several means known in the art (e.g., via computer program). Of course, for a given fin radius R1, the value $\theta$ of the included angle 22 of each fin 18 may have to be adjusted accordingly.

Thus by way of example, for a fixation rod 10 made of titanium with a desired structural rigidity $E_R I_R$ of 6% of that of a bone $E_B I_B$ having an inside radius $R_I$ of 2 mm and an outside radius $R_O$ of 5 mm, computation of the core radius R2 would begin as follows:

$$E_B I_B = \frac{\pi}{4} [(5 \text{ mm})^4 - (2 \text{ mm})^4] E_B$$
$$= (478.3 \text{ mm}^4)(20 \times 10^3 \text{ N/mm}^2)$$
$$= 9.566 \times 10^6 \text{ N-mm}^2$$
$$E_R I_R = (6\%) E_B I_B$$
$$I_R = \frac{(6\%) E_B I_B}{E_R}$$
$$= \frac{(0.06)(9.566 \times 10^6 \text{ N-mm}^2)}{11.03 \times 10^4 \text{ N/mm}^2}$$
$$= 5.2 \text{ mm}^4$$

Once finding the area moment of inertia $I_R$ for the rod 10, the formulas given above can be used to solve for the radius R2 of the core 12 for a given value $\theta$ of included fin angle 22. For example, as is known in the art, iterative computation techniques can be used with a digital computer.

Similarly, solving for the radius R2 of the core 12 for a given value $\theta$ of included fin angle 22 can also be accomplished using the polar moment of inertia $K_R$ for the rod 10, based upon the desired torsional rigidity $K_R G_R$ for the rod 10 (e.g., 6% of the torsional rigidity $K_B G_B$ for the bone).

Detailed information regarding these types of computations and examples thereof can be found in "Formulas for Stress and Strain," by Raymond J. Roark and Warren C. Young (McGraw Hill, 5th ed., 1975), the relevant portions of which are incorporated herein by reference.

By selecting the radius R2 of the core 12 so as to produce a fixation rod 10 having a structural rigidity between 0.1% and 10% of the structural rigidity of the intact bone, the radius R2 of the core 12 typically has a value between ½ and ¼ of the value of the radial extension R1 of the edges 20 of the fins 18, depending upon the fabrication material used. More particularly, the maximum ranges for the fin R1 and core R2 radii are approximately 1 mm–11 mm and 0.5 mm–10 mm, respectively, depending upon the type of bone being treated.

By way of example, for a rod 10 having 6% bending rigidity $E_R I_R$, fin radii R1 of 3 mm, and made from different fabrication materials, typical core radii R2, included fin angles 22, and torsional rigidities $K_R G_R$ are shown below in Table 3:

TABLE 3

Typical Core Radii, Fin Angles and Torsional Rigidities for Rods Having 6% Bending Rigidities and 3 mm Fin Radii

| Rod Material | Core Radius R2 (mm) | Fin Angle (degrees) | Torsional Rigidity |
|---|---|---|---|
| Titanium | 1.65 | 25 | 14% |
| 6AL4V Stainless Steel 316L | 1.50 | 15 | 15% |
| Cobalt Chrome | 0.57 | 18 | 14% |

Thus, by examining the bone sought to be set with the fixation rod 10, the radial extension R1 of the outer edges 20 of the fins 18 can be determined by determining the inside diameter of the cortical bone portion. Then, by selecting the relative structural rigidity (bending and torsional) of the fixation rod 10 (e.g., between 0.1% and 10% of the structural rigidity of the intact bone), the radius R2 of the core 12 can be determined. This results in a fixation rod 10 which can be easily implanted within the medullary canal of the fractured bone by means known in the art and which maintains bending and torsional alignment of the broken bone ends without shielding the fracture site from the natural stresses known to promote and enhance rapid, healthy healing and does not prevent normal endosteal healing or medullary revascularization.

Experiments have been conducted using fixation rods in accordance with the present invention to treat diaphyseally fractured long bones in greyhounds. It was in part from these experiments that the relative structural rigidity range of 0.1% –10% of the structural rigidity of a normal nonfractured bone was determined to be desirable.

Flexible intramedullary fixation rods in accordance with the present invention with structural rigidities ranging from 1.5%–12.9% were implanted in the fractured tibiae of a number of greyhounds. Further in accordance with the present invention, the bending and torsional rigidities ratios of the rods were similar to the bending and torsional rigidities ratios of the greyhounds' intact tibiae. The greyhounds were allowed to walk, i.e., functionally load their tibiae, as tolerated.

From these tests it was learned that the mechanical quality of fracture healing and the rate of fracture healing were not affected by the rods' structural rigidities. The rods with structural rigidities in the high end of the range were surgically less forgiving and therefore more difficult to implant. The rods with structural rigidities in the low end of the range were insufficiently supportive to allow functional loading of the fractured bone without excessive pain. Therefore, for treating the greyhounds' weight-bearing tibiae, structural rigidities in the range of 5%–10% would be optimal.

However, for bones not required to bear weight during the healing process, e.g., those of a human, and particularly smaller bones, rods with low structural rigidities would be acceptable. Therefore, the low end of potentially acceptable structural rigidities can be extended well below the 5% deemed acceptable for the tibiae of greyhounds.

Figure 3A:
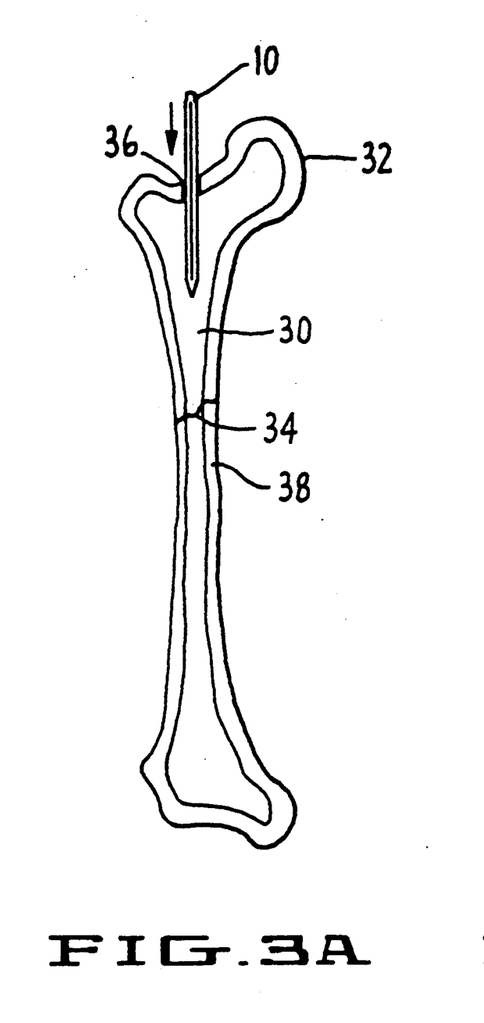
FIG. 3A illustrates a method of implanting the fixation rod in accordance with the present invention through the end of a long bone.
Figure 3B:
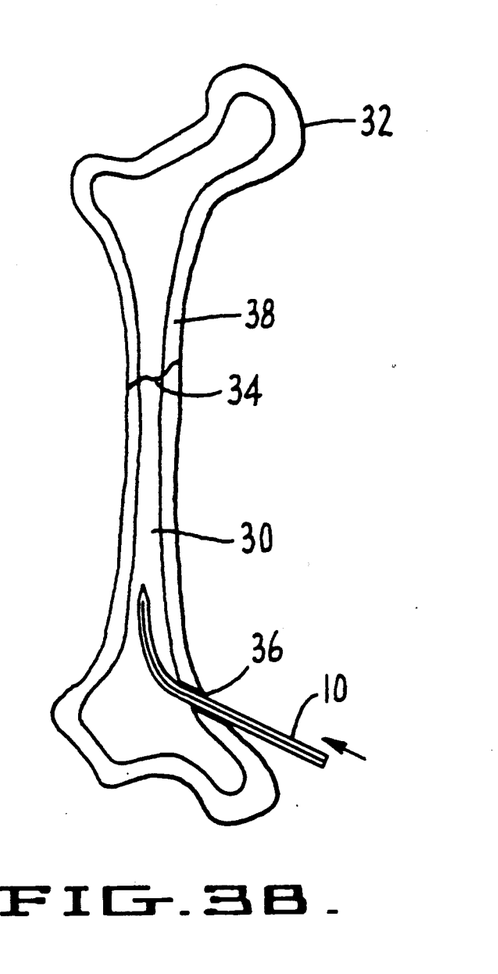
FIG. 3B illustrates a method of implanting the fixation rod in accordance with the present invention through the side of a long bone.

As illustrated in FIGS. 3A–3B, the fixation rod 10 in accordance with the present invention can be easily implanted into the medullary canal 30 of a long bone 32 having a diaphyseal fracture 34. A small pilot hole 36 is drilled in the bone 32 and the fixation rod 10 is implanted therethrough. As described above, the centrally pointed insertion end 14 allows the fixation rod 10 to be driven into the medullary canal 30 without a prior reaming thereof. Also as described above, the dimensional characteristics of the fixation rod 10 are predetermined in accordance with its fabrication material and the inside diameter of the cortical bone structure 38 to allow its easy passage through the medullary canal.

It should be understood that various alternatives to the embodiments of the present invention described herein can be employed in practicing the present invention. It is intended that the following claims define the scope of the present invention and that structures and methods within the scope of these claims and their equivalents be covered thereby.

What is claimed is:

1. A flexible intramedullary fixation rod for insertion into a medullary canal of a bone for treating a diaphyseal fracture thereof, said fixation rod comprising:
   an elongate rod of unitary construction fabricated substantially from a single material and having a bending rigidity B, said rod having:
      an elongate core having a radial periphery at a core radius distal from the longitudinal axis of said core; and
      a plurality of fins radially disposed about said core periphery, each of said fins having an outer fin edge which extends substantially parallel to and along said core longitudinal axis at a fin radius R distal from said core longitudinal axis;
   wherein said core radius and fin radius R are selected to provide said rod with a bending rigidity B within an approximate range according to $(0.001)S \leq B \leq (0.0150)S$ where:
   $S = (\pi/4) [(R+T)^4 - R^4]E$
   $T \in \{3 \text{ mm}, 6 \text{ mm}\}$
   $E = 20{,}000 \text{ N/mm}^2.$ 2. A flexible intramedulary fixation rod as recited in claim 1, wherein said rod has a pointed insertion end and an installation end, and further wherein said fins have substantially triangular cross-sectional areas in a plane normal to said core longitudinal axis.

3. A flexible intramedullary fixation rod as recited in claim 2, wherein said rod fabrication material comprises titanium, said fin radius R is within the approximate range of 1 mm–11 mm and said core radius is within the approximate range of 0.5 mm –10 mm.

4. A flexible intramedullary fixation rod as recited in claim 2, wherein said rod fabrication material comprises stainless steel, said fin radius R is within the approximate range of 1 mm -11 mm and said core radius is within the approximate range of 0.5 mm –10 mm.

5. An improved flexible intramedulary fixation rod for insertion into a medulary canal of a bone for treating a diaphyseal fracture thereof, said rod comprising an elongate member having a maximum radial periphery at a maximum radius allowing said member to be received within said bone medullary canal, and said rod having a length allowing it to extend a substantial distance within said medullary canal on either side of the site of said diaphyseal fracture, said improvement comprising:
   an elongate rod having unitary construction, fabricated from a single material and having an elongate core which is concentric with the longitudinal axis of said elongate rod;
   a plurality of fins radially disposed about the periphery of said elongate rod core, each of said fins having an outer fin edge extending substantially parallel to and along said rod longitudinal axis at a fin radius R distal from said rod longitudinal axis at said elongate member maximum radius; and
   an elongate rod core radius, wherein said core radius and fin radius R are selected to provide said elongate member with a bending rigidity B within an approximate range according to $(0.001)S \leq B \leq (0.150)S$ where:
   $S = (\pi/4) [(R+T)^4 - R^4]E$
   $T \in \{3 \text{ mm}, 6 \text{ mm}\}$
   $E = 20{,}000 \text{ N/mm}^2.$ 6. A flexible intramedullary fixation rod as recited in claim 5, wherein said rod has a pointed insertion end and an installation end, and further wherein said fins have substantially triangular cross-sectional areas in a plane normal to the longitudinal axis of said core.

7. An improved flexible intramedullary fixation rod as recited in claim 6, wherein said fabrication material comprises titanium, said fin radius R is within the approximate range of 1 mm–11 mm and said core radius is within the approximate range of 0.5 mm–10 mm.

8. An improved flexible intramedullary fixation rod as recited in claim 6, wherein said rod fabrication material comprises stainless steel, said fin radius R is within the approximate range of 1 mm–11 mm and said core radius is within the approximate range of 0.5 mm –10 mm.

9. A method for treating a diaphyseal fracture of a bone having an intramedullary canal, said method comprising the steps of:
   determining the radius of an intramedullary canal of a bone having a diaphyseal fracture;
   determining the bending rigidity of said bone;
   selecting a flexible intramedullary fixation rod of unitary construction, fabricated from a single material and having a bending rigidity B, said rod comprising a plurality of fins radially disposed about the periphery of a concentric elongate core, each of said fins having an outer fin edge extending substantially parallel to, along and distal from the longitudinal axis of said concentric elongate core at a fin radius R which is substantially equal to but less than said measured intramedullary canal radius, and said concentric elongate core periphery having a core radius, wherein said core radius and fin radius R are selected to provide said rod with a bending rigidity B within an approximate range according to $(0.001)S \leq B \leq (0.150)S$ where:
   $S = (\pi/4) [(R+T)^4 - R^4]E$
   $T \in \{3 \text{ mm}, 6 \text{ mm}\}$
   $E = 20{,}000 \text{ N/mm}^2;$
   and
   implanting said flexible intramedullary fixation rod into said medullary canal such that said rod extends a substantial distance on either side of said diaphyseal fracture.

10. A method for treating a diaphyseal fracture of a bone having an intramedulary canal, said bone having inherent bending and torsional rigidities prior to said fracture thereof, said method comprising the steps of:

determining the radius of said intramedullary canal;

determining the inherent bending and torsional rigidities of said bone;

selecting a flexible intramedullary fixation rod of unitary construction fabricated from a single material, said rod comprising a plurality of fins radially disposed about the periphery of a concentric core, said fins having outer fin edges extending substantially parallel to and along said rod longitudinal axis at respective fin radii distal from said core longitudinal axis, wherein said fin radii are substantially equal to but less than said measured intramedullary canal radius, and wherein said periphery of said concentric core has a radius selected to provide said fixation rod with bending and torsional rigidities which are less than said inherent bone bending and torsional rigidities, respectively, and further wherein the ratio of said rod bending rigidity to said inherent bone bending rigidity is substantially equal to the ratio of said rod torsional rigidity to said inherent bone torsional rigidity; and implanting said rod into said medullary canal such that said rod extends a substantial distance on either side of said diaphyseal fracture.

* * * * *

UNITED STATES PATENT AND TRADEMARK OFFICE
CERTIFICATE OF CORRECTION

PATENT NO. : 5,053,035

DATED : OCTOBER 1, 1991

INVENTOR(S) : ALEXANDER C. McLAREN

It is certified that error appears in the above - identified patent and that said Letters Patent is hereby corrected as shown below:

In Col. 11, line 32, delete "$(0.001)S<B<(0.0150)S$" and replace with --$(0.001)S<B<(0.150)S$--.

In Col. 11, line 55, delete "medulary" and replace with --medullary--.

In Col. 12, line 13, delete "$S=(\pi/4)[(R+T]^4-R^4]E$" and replace with --$S = (\pi/4)[(R+T)^4-R^4]E$--.

In Col. 12, line 14, delete "$T\varepsilon\{3\ mm,\ 6\ mm]$" and replace with --$T\varepsilon\{3\ mm,\ 6\ mm\}$--.

UNITED STATES PATENT AND TRADEMARK OFFICE
CERTIFICATE OF CORRECTION

PATENT NO. : 5,053,035

DATED : OCTOBER 1, 1991

INVENTOR(S) : ALEXANDER C. McLAREN

It is certified that error appears in the above-indentified patent and that said Letters Patent is hereby corrected as shown below:

In Col. 12, line 68, delete "intramedulary" and insert —intramedullary—.

Signed and Sealed this

Tenth Day of May, 1994

BRUCE LEHMAN

Attest:

Attesting Officer

Commissioner of Patents and Trademarks